US00PP25446P3

(12) United States Plant Patent
Van Rosmalen

(10) Patent No.: US PP25,446 P3
(45) Date of Patent: Apr. 14, 2015

(54) ***PHALAENOPSIS* ORCHID PLANT NAMED 'PHALDAQDAQ'**

(50) Latin Name: ***Phalaenopsis* hybrid**
Varietal Denomination: PHALDAQDAQ

(71) Applicant: Anthura B.V., Bleiswijk (NL)

(72) Inventor: Nicolaas Arnoldus Maria Van Rosmalen, Velp (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 13/987,682

(22) Filed: Aug. 21, 2013

(65) Prior Publication Data

US 2015/0059032 P1 Feb. 26, 2015

(51) Int. Cl.
*A01H 5/00* (2006.01)

(52) U.S. Cl.
USPC ..... Plt./311

(58) Field of Classification Search
USPC ..... Plt./311
See application file for complete search history.

*Primary Examiner* — Annette Para
(74) *Attorney, Agent, or Firm* — Jondle & Associates, P.C.

(57) ABSTRACT

A new and distinct variety of *Phalaenopsis* plant named 'PHALDODIQ', particularly characterized by pink flowers with dark pink dots and white lip, 1 to 2 peduncles, a long and sturdy inflorescence, a narrow obovate leaf shape, and propagated by tissue culture is disclosed.

3 Drawing Sheets

Genus and species: *Phalaenopsis* hybrid.
Variety denomination: 'PHALDODIQ'.

BACKGROUND OF THE NEW PLANT

The present invention comprises a new and distinct cultivar of *Phalaenopsis* plant, botanically known as *Phalaenopsis* of the Orchidaceae family, and hereinafter referred to by the cultivar name 'PHALDODIQ'.

*Phalaenopsis* comprises a genus of about 60 species of herbaceous perennials many of which, or the hybrids thereof, are suitable for cultivar in the home or greenhouse. *Phalaenopsis* is predominantly epiphytic or rock dwelling, and is native to tropical Asia, the Malay Archipelago, and Oceania. The species typically has 2-ranked, fleshy, oblong or elliptic leaves affixed to a short central stem (monopodial growth), which vary in size from 12 to 20 cm to over 60 cm. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petals, called the labellum, is three-lobed and is often more brightly-colored than the other flower segments. Flower colors include various shades of pink, white, yellow, and red-brown.

*Phalaenopsis* orchids are typically propagated from seeds. Asexual propagation of *Phalaenopsis* is often done from off-shoots which arise from the lower bracts of the inflorescence. The resulting plants are detached from the mother plants and may be planted in a suitable substrate.

The new *Phalaenopsis* 'PHALDODIQ' is particularly characterized by its attractive and unique pink flowers with unique white lip, economical propagation by tissue culture, rapid growth, and a plant dimension suitable for packaging and shipping to the market.

'PHALDODIQ' is a product of a planned breeding program conducted in Bleiswijk, The Netherlands.

The new *Phalaenopsis* 'PHALDODIQ' originated from a cross made in February 2005 in Bleiswijk, The Netherlands. The female parent is a pink with a white lip *Phalaenopsis* pot plant name '22768-01' (unpatented), while the male parent is a lilac with a white lip *Phalaenopsis* pot plant named '22763-02' (unpatented). A single plant was selected in April 2008 and has been asexually reproduced repeatedly by meristem tissue culture in Bleiswijk, The Netherlands over a 5-year period. The new variety has been found to retain its distinctive characteristics through successive asexual propagations.

Asexual reproduction of 'PHALDODIQ' by tissue culture was first performed in April 2011 in Bleiswijk, The Netherlands and has demonstrated that the new cultivar is firmly fixed and retained through successive generations of asexual reproduction.

Plant Breeder's Rights for this variety have been applied for in Europe on Jan. 15, 2013. 'PHALDODIQ' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands.

1) Pink flower with dark pink dots and white lip;
2) 1 to 2 peduncles;
3) Inflorescence is long and sturdy;
4) The shape of the leaf is narrow obovate; and
5) Plants are propagated by tissue culture.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs are of a 50-week old plant grown in a greenhouse in Bleiswijk, The Netherlands in March 2013.

DESCRIPTION OF THE NEW VARIETY

Figure 1:
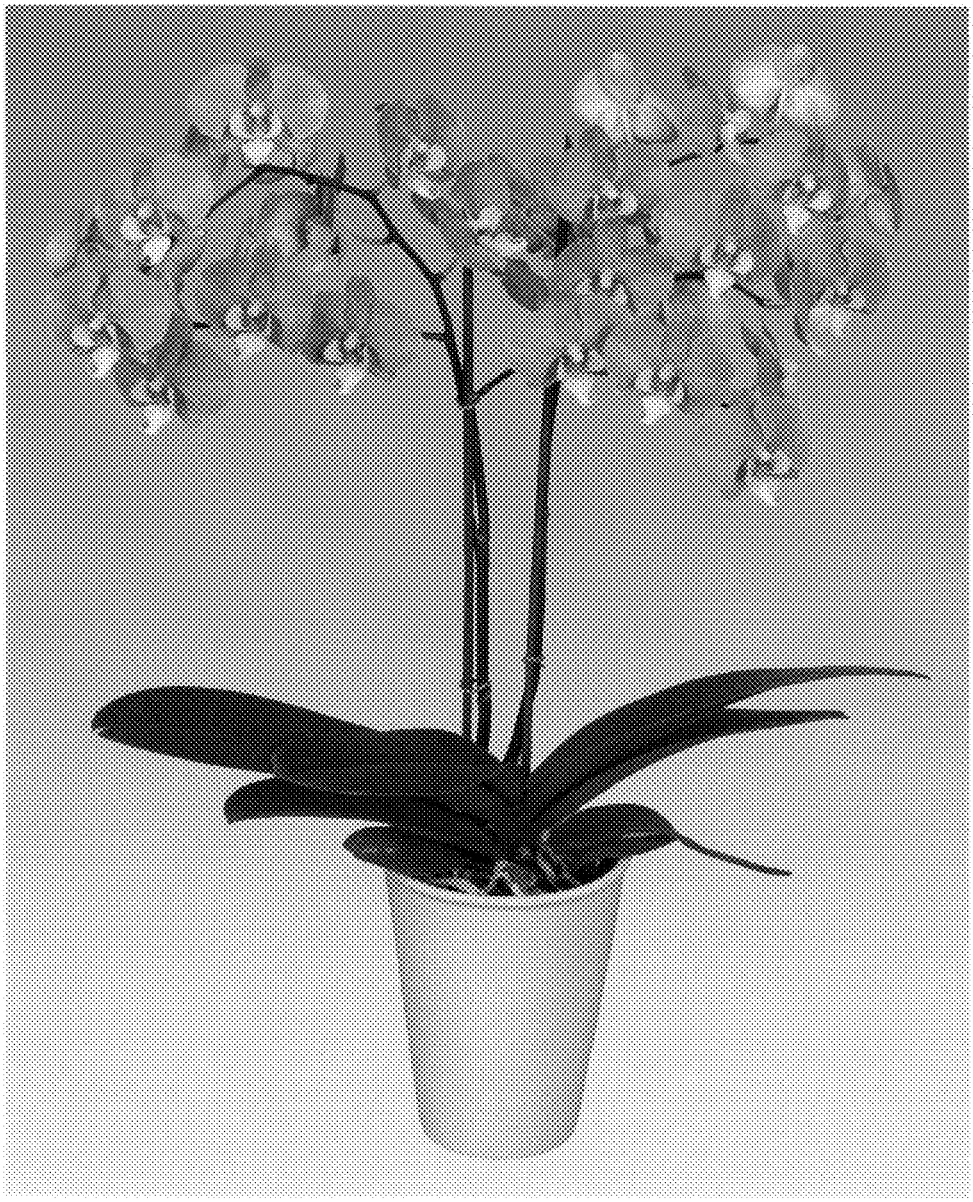
FIG. 1 shows the overall plant habit, including blooms, buds and foliage of 'PHALDODIQ'.
Figure 2:
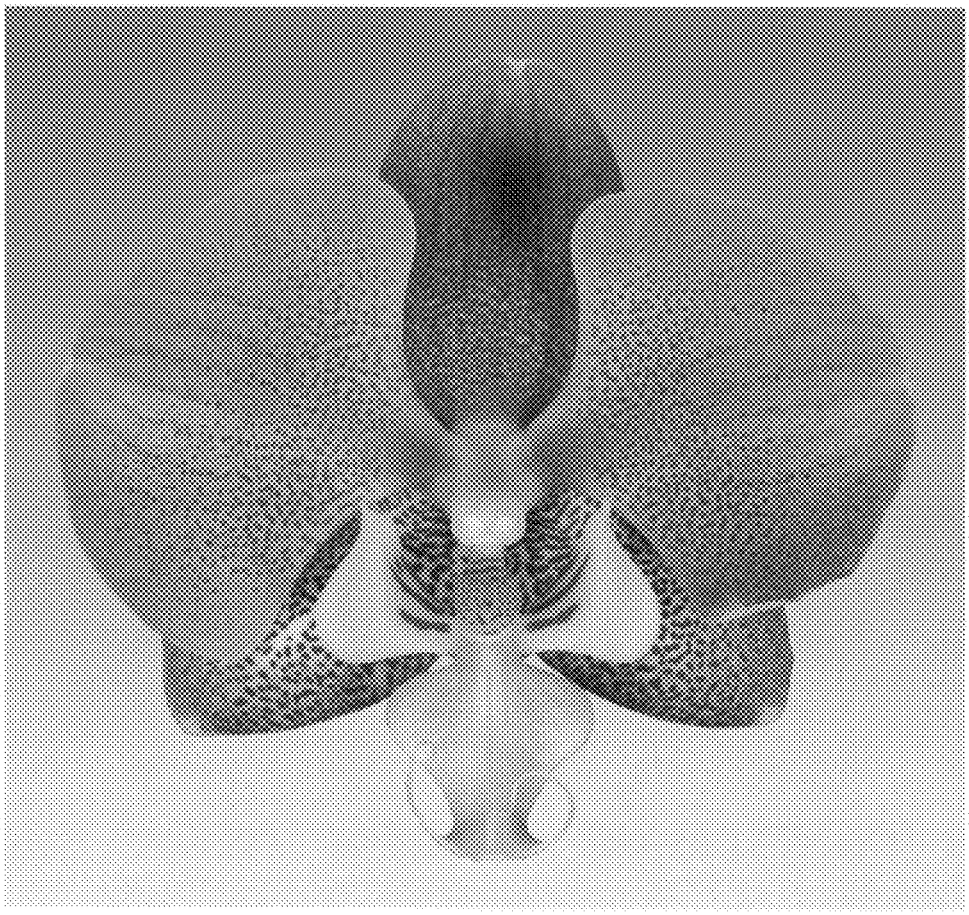
FIG. 2 shows a close-up of the flower of 'PHALDODIQ'.
Figure 3:
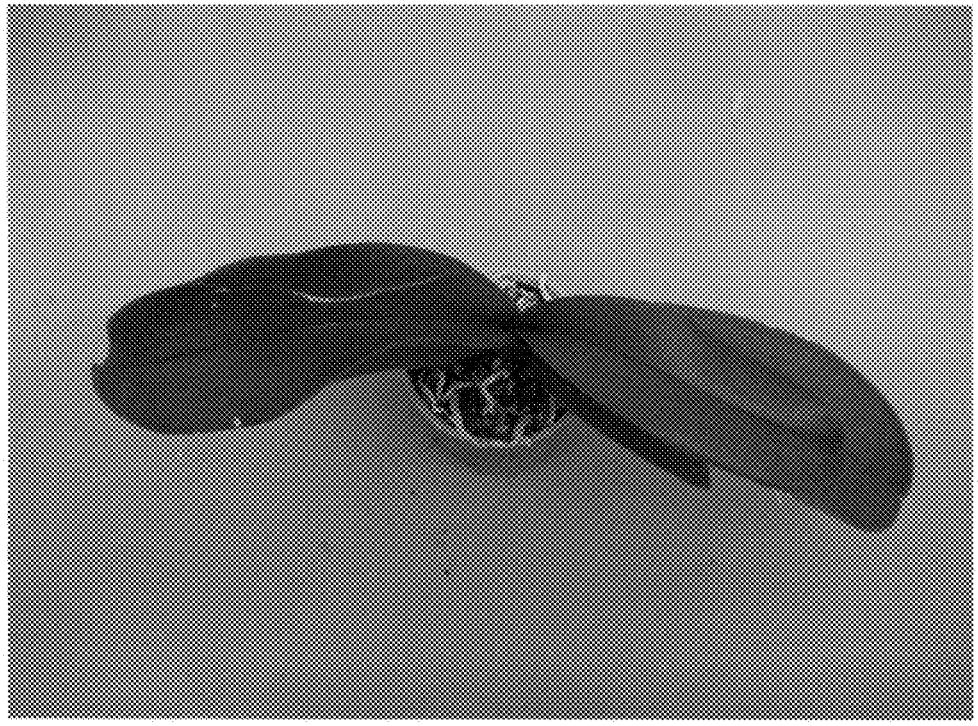
FIG. 3 shows a close-up of the leaves of 'PHALDODIQ'.

The following detailed description sets forth the distinctive characteristics of 'PHALDODIQ'. The data which define these characteristics were collected from asexual reproductions carried out in Bleiswijk, The Netherlands. The plant history was taken on 50-week old plants which were planted from tissue culture in 12 centimeter pots and grown in a greenhouse between 27° C. to 29° C. for 30 weeks, continued by a cooling period of 8 weeks between 18° C. to 20° C. and 12 weeks in a greenhouse of 21° C. Observations were made in March 2013. Color readings were taken under 4000 till 6000 lux natural light in the greenhouse. Color references are primarily to The R.H.S. Colour Chart of The Royal Horticultural Society of London (R.H.S.) (2001).

DETAILED BOTANICAL DESCRIPTION

Classification:

*Family.*—Orchidaceae.

*Botanical.*—*Phalaenopsis* hybrid.

*Common name.*—*Phalaenopsis.*

*Variety name.*—'PHALDODIQ'.

Parentage:

*Female parent.*—*Phalaenopsis* cultivar '22768-01' (unpatented).

*Male parent.*—*Phalaenopsis* cultivar '22763-02' (unpatented).

Propagation:

*Type.*—Tissue culture (meristem).

Plant:

*Crop time* (*time to produce a finished flowering plant*) .—48 to 50 weeks for a 12 cm pot.

*Growth habit of inflorescence.*—Standard type, green leaves and normal raceme.

*Height* (*including pot, including inflorescence*).—60.0 cm to 65.0 cm.

*Width* (*measured from leaf tips*).—43.0 cm to 48.0 cm.

*Vigor.*—Strong.

Roots:

*Root description.*—Grey-green-colored roots with light branching lateral roots having grey-green-colored root tips.

Leaves:

*Mature leaves.*—Quantity per plant: 5 to 6 leaves are produced before flowering. Length (fully expanded): 21.0 cm to 24.0 cm. Width: 7.5 cm to 8.5 cm. Shape: Narrow obovate. Apex: Mucronate. Base: Moderately elongated. Leaf blade angle with the petiole: Between 20 degrees and 45 degrees. Leaf margin: Entire. Color: Upper surface: RHS 137A. Lower surface: RHS 138B. Texture: Smooth and slightly rough. Thickness: 2.5 mm. Venation: Pattern: Parallel. Color of the midvein: Upper surface: RHS 139A. Lower surface: RHS 139C.

Peduncle:

*Quantity per plant.*—1 to 2.

*Number of flowers per peduncle.*—14 to 20.

*Length.*—55.0 cm.

*Diameter.*—About 7.0 mm.

*Strength.*—Strong.

*Aspect.*—Upright.

*Texture.*—Smooth.

*Color.*—Brown/dark green (between RHS 200A and RHS 147A).

*Internode length.*—50.0 mm to 90.0 mm.

Inflorescence description:

*Appearance.*—Upright to slightly pendant, raceme inflorescence with bilaterally symmetrical flowers that open in succession beginning with the lowermost flower.

*Inflorescence size.*—Height (from base to tip): 80.0 mm to 110.0 mm. Diameter: 150.0 mm to 200.0 mm.

*Flowering time.*—First flowers can be expected 10 to 11 months after planting in a 12 cm pot.

*Flower.*—Height: 50.0 mm to 60.0 mm. Diameter: 70.0 mm to 80.0 mm. Depth of lip: 22.0 mm to 24.0 mm.

*Flower longevity.*—On the plant: 10 to 14 weeks.

*Fragrance.*—Absent.

*Petals.*—Arrangement: Open. Shape: Semi-circular. Apex: Mucronate and symmetric. Margin: Entire and slightly undulate. Length: 39.0 mm to 43.0 mm. Width: 31.0 mm to 35.0 mm. Color (when fully opened): Main color: Pink with purple dots (RHS 80B; 78A). At the base: Pink (RHS 78B).

*Dorsal sepal.*—Shape: Elliptic. Length: 29.0 mm to 33.0 mm. Width: 19.0 mm to 23.0 mm. Color (when fully opened): Main color: Pink with purple dots (RHS 80B; 78A). At the base: Pink (RHS 78B).

*Lateral sepals.*—Shape: Ovate. Length: 18.0 mm to 22.0 mm. Width: 28.0 mm to 32.0 mm. Color (when fully opened): Main color: Pink with lighter center and purple dots (RHS 80B; 75D; 78A). At the base: Light pink with a touch of green and dark purple dots (RHS 75D; 150C; 77A).

*Labellum* (*lip*).—Margin: Entire and slightly undulate. Length: 23.0 mm to 25.0 mm. Width: 24.0 mm to 26.0 mm.

*Lateral lobe.*—Shape: type V. Color: White with red stripes (RHS 155C; 59B).

*Apical lobe.*—Shape: Obdeltoid. Color: White with light pink shade and purple spots (RHS 155C; 76C; 78A).

*Callus.*—Color: Orange with purple dots (RHS 21A; 59B).

*Callosities.*—None.

*Pedicel.*—Length: 30.0 mm to 34.0 mm. Diameter: 2.5 mm to 3.5 mm.

Reproductive organs:

*Arrangement.*—The stamens, style and stigmas are fused into a single, short structure called the column, possessing one terminal anther with pollen grains united into pollinia, which are covered by an anther cap. The stigma is located under the column behind the pollinia. The ovary is inferior with three carpels present.

*Column.*—Length: 10.0 mm to 11.0 mm. Diameter: 5.5 mm. Color: Light pink (RHS 76A).

*Pollinia.*—Quantity: 2. Size: 1.3 mm to 1.4 mm. Color: Orange (RHS 26A).

*Ovary*.—Length: 9.0 mm to 10.0 mm. Diameter: 4.0 mm to 5.0 mm.

Disease, pest, and stress resistance: No specific resistance or susceptibility observed.

Temperature tolerance: Tolerant to a low temperature of 15° C. and a high temperature about 30° C.

COMPARISON WITH PARENTAL AND COMMERCIAL VARIETIES

'PHALDODIQ' differs from female parent '22768-01' (unpatented) in that '22768-01' has a flower that is darker and more even than that of 'PHALDODIQ'.

'PHALDODIQ' differs from male parent '22763-02' (unpatented) in that '22763-02' has a flower that has a flush of larger over color, whereas 'PHALDODIQ' does not.

'PHALDODIQ' differs from commercial variety 'PHALBATZOM' (unpatented) in that 'PHALBATZOM' has a darker, more even flower color than 'PHALDODIQ'. In addition, 'PHALBATZOM' has dark red/purple lip, whereas 'PHALDODIQ' has a white lip.

I claim:

1. A new and distinct variety of *Phalaenopsis* plant named 'PHALDODIQ' as shown and described herein.

* * * * *

UNITED STATES PATENT AND TRADEMARK OFFICE

CERTIFICATE OF CORRECTION

PATENT NO. : PP25,446 P3
APPLICATION NO. : 13/987682
DATED : April 14, 2015
INVENTOR(S) : Nicolaas Van Rosmalen It is certified that error appears in the above-identified patent and that said Letters Patent is hereby corrected as shown below:

Title page, item (54), the title of the invention currently reads:

*PHALAENOPSIS* ORCHID PLANT NAMED "'PHALDAQDAQ'"

The title of the invention should read:

*PHALAENOPSIS* ORCHID PLANT NAMED --'PHALDODIQ'--

Title page, item (50), the Varietal Denomination currently reads:

Varietal Denomination: "PHALDAQDAQ"

The Varietal Denomination should read:

Varietal Denomination: --'PHALDODIQ'--

Signed and Sealed this
Eighteenth Day of August, 2015

Michelle K. Lee

Michelle K. Lee
*Director of the United States Patent and Trademark Office*